(12) United States Patent
Liu et al.

(10) Patent No.: US 11,808,751 B2
(45) Date of Patent: Nov. 7, 2023

(54) METHOD AND SYSTEM FOR DETECTING MASS OF OIL IN INORGANIC MINERAL OF SHALE

(71) Applicant: Northeast Petroleum University, Daqing (CN)

(72) Inventors: Bo Liu, Daqing (CN); Shansi Tian, Daqing (CN); Xiaofei Fu, Daqing (CN); Fang Zeng, Daqing (CN); Zhiwei Hu, Daqing (CN); Liu Wang, Daqing (CN); Ning Hou, Daqing (CN)

(73) Assignee: Northeast Petroleum University, Daqing (CN)

( * ) Notice: Subject to any disclaimer, the term of this patent is extended or adjusted under 35 U.S.C. 154(b) by 562 days.

(21) Appl. No.: 17/031,324

(22) Filed: Sep. 24, 2020

(65) Prior Publication Data
US 2022/0057379 A1 Feb. 24, 2022

(30) Foreign Application Priority Data
Aug. 24, 2020 (CN) .......................... 202010856006.4

(51) Int. Cl.
*G01N 33/24* (2006.01)
*G01N 1/40* (2006.01)
(Continued)

(52) U.S. Cl.
CPC ......... *G01N 33/241* (2013.01); *G01N 1/4055* (2013.01); *G01N 5/04* (2013.01);
(Continued)

(58) Field of Classification Search
CPC ...... G01N 33/241; G01N 1/4055; G01N 5/04; G01N 23/20; G01N 2223/056; C10G 32/00
See application file for complete search history.

(56) References Cited

U.S. PATENT DOCUMENTS

2012/0100588 A1* 4/2012 Wallage ................. C10G 32/00
435/166
2019/0056374 A1* 2/2019 Rocher .................. G01N 33/24
(Continued)

FOREIGN PATENT DOCUMENTS

CN        103487310 A   *  1/2014
CN        108982286 A1  * 12/2018  ............... G01N 5/04
(Continued)

OTHER PUBLICATIONS

M.D.Lewan "Experiments on the role of water in petroleum formation", pp. 6391-3723 US Geological Survey, Apr. 25, 1997 (Year: 1997).*

*Primary Examiner* — Michael J Dalbo
*Assistant Examiner* — Kaleria Knox
(74) *Attorney, Agent, or Firm* — Wood Herron & Evans LLP

(57) ABSTRACT

A system is provided for detecting the mass of oil in an inorganic mineral of shale. The system operates by performing an extraction test on a first shale sample by using chloroform to obtain a total content of shale oil in the shale; enriching kerogen from the second shale sample to obtain dry kerogen; and performing an extraction test on oven-dried kerogen by using chloroform to determine the mass of extracted kerogen. The system also operates by determining the mass of the oil in the organic matter of the shale sample and the mass of the oil in an inorganic mineral of the shale; establishing a model for predicting a ratio of the mass of the oil in the inorganic mineral of the shale to the mass of the oil in the organic matter; and using the prediction model to determine the mass of oil in an inorganic mineral.

6 Claims, 5 Drawing Sheets

(51) Int. Cl.
*G01N 5/04* (2006.01)
*G01N 23/20* (2018.01)

(52) U.S. Cl.
CPC ..... *G01N 23/20* (2013.01); *G01N 2001/4061* (2013.01); *G01N 2223/056* (2013.01)

(56) References Cited

U.S. PATENT DOCUMENTS

2020/0173902 A1* 6/2020 Wang ................ G01N 15/08
2022/0059191 A1* 2/2022 Tian ................. G16C 10/00

FOREIGN PATENT DOCUMENTS

CN           111027882 A * 4/2020 ............. G06N 3/084
WO    WO-2019157413 A1 * 8/2019 ........... E21B 49/005

* cited by examiner

METHOD AND SYSTEM FOR DETECTING MASS OF OIL IN INORGANIC MINERAL OF SHALE

CROSS-REFERENCE TO RELATED APPLICATION

This application claims priority to Chinese Application No. 202010856006.4, filed Aug. 24, 2020. The above-mentioned patent application is incorporated herein by reference in its entirety.

TECHNICAL FIELD

This application relates to petroleum geological exploration, and in particular, to a system and method for detecting the mass of oil in an inorganic mineral.

BACKGROUND

Shale has the potential to become an oil reservoir. The effective mobility and flow of oil in the shale are related to the size, structure, distribution and connectivity of the pore throat of the shale, as well as the liquid-solid interactions and the occurrence states (such as adsorbed, free and dissolved) and mechanisms of oil in the reservoirs. Therefore, the effective mobility and flow of shale oil are further related to the composition, types and physical properties of shale oil, such as viscosity and density.

The occurrence states (dissolved, swelling, adsorbed and free) of shale oil, the proportion of the occurrence states, the pore size of occurrence and the mutual conversion conditions (i.e. the occurrence mechanism of shale oil) are closely related to the mobility of shale oil. Due to the low water content in shale and the extremely low solubility of oil in water, the dissolved shale oil is ignored in the study of shale oil occurrence. The swelling shale oil occurs in the organic matter, where the shale oil molecules are "surrounded" by kerogen molecules, making the swelling shale oil the most difficult to flow. The adsorbed oil is adsorbed on the surface of the organic matter and mineral particles in a "solid-like" state, and its mobility is superior to that of the swelling shale oil. The free shale oil is not subjected to the adsorption by the kerogen and mineral particles, and is the most easy to flow. There are three occurrence states of oil in the organic matter of shale, namely swelling, adsorbed and free states. Among them, the swelling and adsorbed states are dominant, resulting in the poor mobility of the oil in the organic matter. The oil in the inorganic minerals of shale have only two occurrence states, adsorbed and free states. As the free state is dominant, the oil in the inorganic minerals is highly mobile. The oil in the inorganic minerals of shale can be quantitatively evaluated to improve the accuracy of shale oil mobility evaluation. However, at present, it is not possible to distinguish the oil in the inorganic mineral of shale from the oil in the organic matter of shale by using chloroform bitumen. Therefore, it is impossible to detect the mass of oil in the inorganic mineral of shale in different evolution stages.

As such, it would be desirable to provide a method and system for detecting the mass of oil in an inorganic mineral of shale.

SUMMARY

In accordance with embodiments of the invention, a method is provided that distinguishes the oil in the inorganic mineral of the shale from the oil in an organic matter of the shale and improves the accuracy of shale oil mobility evaluation.

In one embodiment, a method for detecting the mass of oil in an inorganic mineral of shale includes: obtaining a shale sample and determining a parameter of the shale sample; dividing the shale sample into a first shale sample and a second shale sample, and performing an extraction test on the first shale sample by using chloroform to obtain a total content of shale oil in the shale; enriching kerogen from the second shale sample to obtain dry kerogen; oven-drying the dry kerogen to obtain oven-dried kerogen and determining the mass of the oven-dried kerogen; performing an extraction test on the oven-dried kerogen by using chloroform and determining the mass of extracted kerogen; determining a difference between the mass of the oven-dried kerogen and the mass of the extracted kerogen as the mass of oil in an organic matter; multiplying a ratio of the mass of the oil in the organic matter to the mass of the second shale sample by 100 to obtain the mass of the oil in the organic matter of the shale sample; subtracting the mass of the oil in the organic matter of the shale sample from the total content of the shale oil in the shale to obtain the mass of the oil in the inorganic mineral of the shale; fitting the ratio of the mass of the oil in the inorganic mineral of the shale to the mass of the oil in the organic matter of the shale sample and the parameter of the shale sample to establish a model for predicting the ratio of the mass of the oil in the inorganic mineral of the shale to the mass of the oil in the organic matter; obtaining the mass of oil in an organic matter of shale to be detected; and using the prediction model to determine the mass of the oil in an inorganic mineral of the shale to be detected according to the mass of the oil in the organic matter of the shale to be detected.

In some embodiments, the parameter includes a mineral composition ratio, a total organic carbon (TOC) content, a vitrinite reflectance (VR) and a porosity; the mineral composition ratio is derived by performing whole-rock X-ray diffraction (XRD) on the shale sample; the mineral composition ratio includes a quartz ratio, a clay mineral ratio and a carbonate mineral ratio.

In another embodiment, the enriching kerogen from the second shale sample specifically includes: enriching the kerogen in the second shale sample by using a sedimentary rock kerogen separation method.

In one embodiment, the oven-drying the dry kerogen specifically includes: drying the dry kerogen by using an oven at 110° C. for 6 h.

In yet another embodiment, the prediction model is calculated by:

$$W_{inorganic/organic} = \frac{1}{\sqrt{2\pi} \cdot (d_1 + d_2)} (M_{TOC} \cdot TOC + M_q \cdot \text{Quanrtz} + M_c \cdot \text{Clay} + M_0 \cdot \text{Other}) \cdot \text{EXP}\left[-\left(\frac{\ln R_0 - a}{d_1}\right)^2 - \left(\frac{\ln \Phi - b}{d_2}\right)^2\right]$$

where, $W_{inorganic/organic}$ indicates a ratio of the mass of the oil in the inorganic mineral of the shale to the mass of the oil in the organic matter of the shale sample; TOC indicates a total organic carbon content; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient;

Other indicates other ratios, such as a carbonate mineral ratio; $R_o$ indicates a VR; a indicates a first VR coefficient; $d_1$ indicates a second VR coefficient; Φ indicates a porosity; b indicates a first porosity coefficient; $d_2$ indicates a second porosity coefficient.

In another embodiment, the using the prediction model to determine the mass of the oil in an inorganic mineral of the shale to be detected according to the mass of the oil in the organic matter of the shale to be detected specifically includes:

determining the mass of the oil in the inorganic mineral of the shale to be detected according to the following formula:

$$Q_{inorganic} = Q_{organic} \times W_{inorganic/organic}$$

where, $Q_{inorganic}$ indicates the mass of the oil in the inorganic mineral of the shale to be detected, and $Q_{organic}$ indicates the mass of the oil in the organic matter of the shale to be detected.

According to further embodiments, a system for detecting the mass of oil in an inorganic mineral of shale includes: a shale sample obtaining module, configured to obtain a shale sample and determine a parameter of the shale sample; a total shale oil content determination module, configured to divide the shale sample into a first shale sample and a second shale sample and perform an extraction test on the first shale sample by using chloroform to obtain a total content of shale oil in the shale; an enrichment module, configured to enrich kerogen from the second shale sample to obtain dry kerogen; an oven-dried kerogen mass determination module, configured to oven-dry the dry kerogen to obtain oven-dried kerogen and determine the mass of the oven-dried kerogen; an extracted kerogen mass determination module, configured to perform an extraction test on the oven; dried kerogen by using chloroform and determine the mass of extracted kerogen; an organic matter-occurring oil mass determination module, configured to determine a difference between the mass of the oven-dried kerogen and the mass of the extracted kerogen as the mass of oil in an organic matter; a shale sample organic matter-occurring oil mass determination module, configured to multiply a ratio of the mass of the oil in the organic matter to the mass of the second shale sample by 100 to obtain the mass of the oil in the organic matter of the shale sample; a shale inorganic mineral-occurring oil mass determination module, configured to subtract the mass of the oil in the organic matter of the shale sample from the total content of the shale oil in the shale to obtain the mass of the oil in the inorganic mineral of the shale; a prediction model establishment module, configured to fit the ratio of the mass of the oil in the inorganic mineral of the shale to the mass of the oil in the organic matter of the shale sample and the parameter of the shale sample to establish a model for predicting the ratio of the mass of the oil in the inorganic mineral of the shale to the mass of the oil in the organic matter; a to-be-detected shale organic matter-occurring oil mass obtaining module, configured to use the prediction model to determine the mass of the oil in an organic matter of shale to be detected; and a to-be-detected shale inorganic mineral-occurring oil mass determination module, configured to use the prediction model to determine the mass of the oil in an inorganic mineral of the shale to be detected according to the mass of the oil in the organic matter of the shale to be detected.

In one embodiment, the parameter includes a mineral composition ratio, a TOC content, a VR and a porosity; the mineral composition ratio includes a quartz ratio, a clay mineral ratio and a carbonate mineral ratio.

In another embodiment, the prediction model is calculated by:

$$W_{inorganic/organic} = \frac{1}{\sqrt{2\pi} \cdot (d_1 + d_2)} (M_{TOC} \cdot TOC + M_q \cdot Quanrtz + M_c \cdot Clay + M_0 \cdot Other) \cdot EXP\left[-\left(\frac{\ln R_0 - a}{d_1}\right)^2 - \left(\frac{\ln \Phi - b}{d_2}\right)^2\right]$$

where, $W_{inorganic/organic}$ indicates a ratio of the mass of the oil in the inorganic mineral of the shale to the mass of the oil in the organic matter of the shale sample; TOC indicates a total organic carbon content; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient; Other indicates other ratios, such as a carbonate mineral ratio; $R_o$ indicates a VR; a indicates a first VR coefficient; $d_1$ indicates a second VR coefficient; Φ indicates a porosity; b indicates a first porosity coefficient; $d_2$ indicates a second porosity coefficient.

In some embodiments, the to-be-detected shale inorganic mineral-occurring oil mass determination module specifically includes: a to-be-detected shale inorganic mineral-occurring oil mass determination unit, configured to determine the mass of the oil in the inorganic mineral of the shale to be detected according to the following formula:

$$Q_{inorganic} = Q_{organic} \times W_{inorganic/organic}$$

where, $Q_{inorganic}$ indicates the mass of the oil in the inorganic mineral of the shale to be detected, and $Q_{organic}$ indicates the mass of the oil in the organic matter of the shale to be detected.

Compared with known methods and systems, embodiments of the present invention achieve the following beneficial effects.

The present invention proposes a method and system for detecting the mass of oil in an inorganic mineral of shale. The method includes: dividing a shale sample into a first shale sample and a second shale sample, and performing an extraction test on the first shale sample by using chloroform to obtain a total content of shale oil in the shale; enriching kerogen from the second shale sample to obtain dry kerogen; oven-drying the dry kerogen, performing an extraction test on the oven-dried kerogen by using chloroform, determining the mass of extracted kerogen, and finally obtaining the mass of oil in an organic matter of the shale sample and the mass of oil in an inorganic mineral of the shale; establishing a model for predicting a ratio of the mass of the oil in the inorganic mineral of the shale to the mass of oil in the organic matter of the shale; and using the model to detect the mass of oil in an inorganic mineral of shale to be detected. The present invention solves the problem that the conventional chloroform bitumen method cannot distinguish the oil in the inorganic mineral of the shale from the oil in the organic matter of the shale. Therefore, the present invention improves the accuracy of shale oil mobility evaluation.

BRIEF DESCRIPTION OF THE DRAWINGS

The features and advantages of the invention will be appreciated upon reference to the following drawings. The accompanying drawings, which are incorporated in and constitute a part of this specification, illustrate one or more embodiments of the invention and, together with the general description given above and the detailed description given below, explain the one or more embodiments of the invention.

DETAILED DESCRIPTION

The technical solutions in the examples of the present invention are clearly and completely described with reference to the accompanying drawings in the examples of the present invention. Apparently, the described examples are merely a part rather than all of the examples of the present invention. All other examples obtained by a person of ordinary skill in the art based on the examples of the present invention without creative efforts should fall within the protection scope of the present invention.

An objective of the present invention is to provide a method and system for detecting the mass of oil in an inorganic mineral of shale. The present invention in the embodiments described distinguishes the oil in the inorganic mineral of the shale from the oil in an organic matter of the shale and improves the accuracy of shale oil mobility evaluation.

In order to make the above objectives, features, and advantages of the present invention clearer and more comprehensible, the present invention is described in further detail below with reference to the accompanying drawings and specific implementations.

Figure 1:
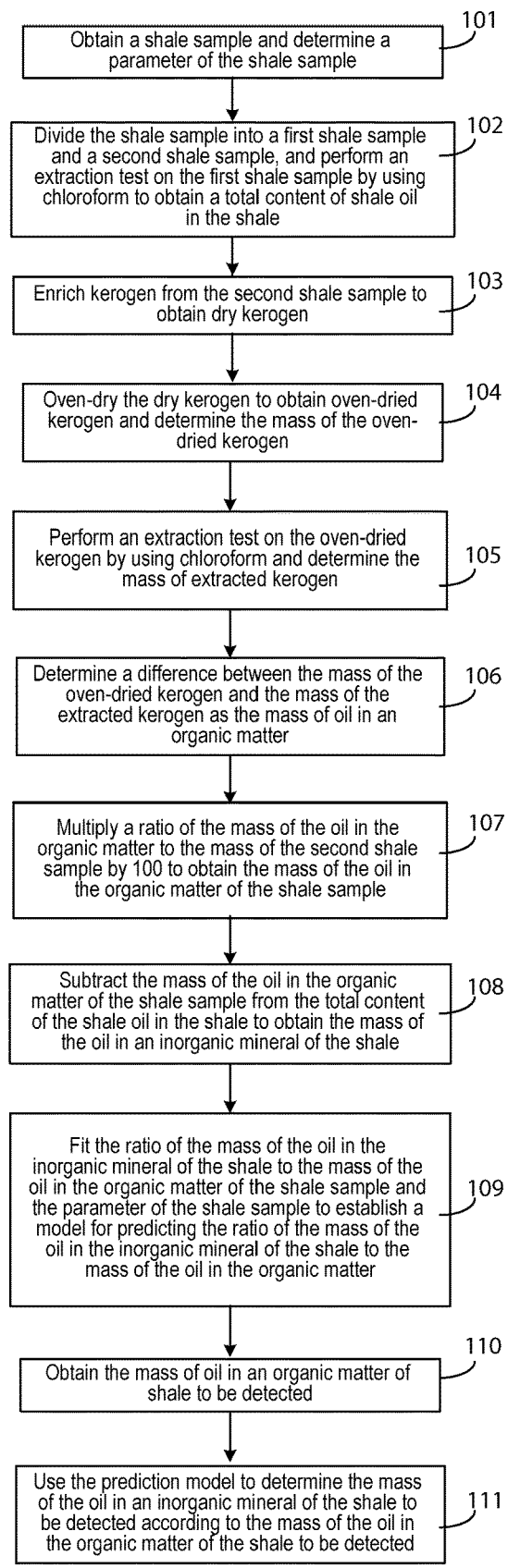
FIG. 1 is a flowchart of a method for detecting the mass of oil in an inorganic mineral of shale according to embodiments of the present invention.

FIG. 1 is a flowchart of a method for detecting the mass of oil in an inorganic mineral of shale according to an example of the present invention. As shown in FIG. 1, a method for detecting the mass of oil in an inorganic mineral of shale includes: Step 101: obtain a shale sample and determine a parameter of the shale sample.

The parameter includes a mineral composition ratio, a total organic carbon (TOC) content, a vitrinite reflectance (VR) and a porosity; the mineral composition ratio includes a quartz ratio, a clay mineral ratio, a carbonate mineral ratio and a heavy mineral ratio.

300-400 g of representative shale sample from a target area was subjected to a whole-rock X-ray diffraction (XRD) test. The test results of 15 samples are shown in Table 1.

TABLE 1

Inorganic mineral composition of 15 samples

| Well No. | Depth | Quartz | Clay mineral | Potash feldspar | Plagioclase |
|---|---|---|---|---|---|
| Gu 204 | 2376 | 37.97 | 39.93 | | 12.23 |
| Gu 844 | 2579 | 37.06 | 36.93 | 0.45 | 14.71 |
| Ying 391 | 2166 | 20.18 | 13.36 | | 35.65 |
| Ying 52 | 2187.3 | 41.44 | 36.01 | 2.41 | 19.21 |

TABLE 1-continued

Inorganic mineral composition of 15 samples

| Ying 52 | 2189 | 36.11 | 41.21 | 0.72 | 13.49 |
|---|---|---|---|---|---|
| Ying 52 | 2190.35 | 37.95 | 34.32 | | 16.61 |
| Ying 52 | 2190.6 | 23.07 | 23.94 | | 7.67 |
| Tai 602 | 1821 | 35.08 | 43.65 | | 14.92 |
| Tai 602 | 1825.5 | 33.88 | 41.06 | | 17.2 |
| Tai 602 | 1827 | 33.43 | 45.73 | | 16.97 |
| Xu 11 | 1948 | 33.25 | 38.73 | 1.12 | 13.56 |
| Xu 11 | 1965.47 | 32.65 | 38.58 | 1.81 | 20.13 |
| Xu 11 | 1966.27 | 30.66 | 39.85 | | 14.87 |
| Xu 11 | 1972 | 11.51 | 12.24 | | 2.17 |
| Xu 11 | 1996.17 | 40.35 | 39.21 | | 7.25 |

| Well No. | Calcite | Ferrodolomite | Dolomite | Siderite | Pyrite |
|---|---|---|---|---|---|
| Gu 204 | 1.43 | 6.96 | | 1.48 | |
| Gu 844 | 3.36 | | | | 7.48 |
| Ying 391 | 24.82 | 4.84 | | | 1.15 |
| Ying 52 | 0.93 | | | | |
| Ying 52 | 1.55 | 6.92 | | | |
| Ying 52 | 4.57 | 1.71 | | 1.23 | 3.61 |
| Ying 52 | 5.35 | | | | 39.96 |
| Tai 602 | | | | | 6.35 |
| Tai 602 | | 1.12 | | 1.71 | 5.03 |
| Tai 602 | 3.86 | | | | |
| Xu 11 | 4.09 | 4.45 | | | 4.81 |
| Xu 11 | 0.81 | 0.44 | | 1.04 | 4.54 |
| Xu 11 | 9.06 | | | 1.8 | 3.77 |
| Xu 11 | | | 74.08 | | |
| Xu 11 | 8.49 | | | 0.42 | 4.28 |

Step 102: divide the shale sample into a first shale sample and a second shale sample, and perform an extraction test on the first shale sample by using chloroform to obtain a total content of shale oil in the shale.

The representative shale sample from the target area was crushed into 80-120 meshes, and then divided into two samples. The mass of a first sample was measured as ⅓ of the total mass, and recorded as $m_1$ (unit, g). An extraction test was performed on the first sample by using chloroform to obtain chloroform bitumen "A" in the shale, which was referred to as total "A" (unit, %) to represent a total content of shale oil in the shale, that is, a sum of oil in an inorganic mineral of the shale and the mass of oil in an organic matter of the shale. The mass of a second sample was measured as ⅔ of the total mass, and recorded as $m_2$ (unit, g).

Step 103: enrich kerogen from the second shale sample to obtain dry kerogen.

Kerogen in the second shale sample was enriched by using a sedimentary rock kerogen separation method (i.e. a method as specified by GB/T 19144-2010). By acid-treating the second shale sample, an inorganic mineral was dissolved, and the kerogen was enriched. It should be noted that in step 6.7 of the kerogen enrichment test as per the GB/T 19144-2010 standard, chloroform was not used to clean the dry, fine-grained kerogen, but step 104 was performed after step 6.6.

Step 104: oven-dry the dry kerogen to obtain oven-dried kerogen and determine the mass of the oven-dried kerogen.

The enriched kerogen was dried by using an oven at 110° C. for 6 h to remove moisture from the enriched kerogen. Then the oven-dried kerogen was taken out and weighed, and the mass of the dried kerogen was measured as $m_{k1}$ (unit, g).

Step 105: perform an extraction test on the oven-dried kerogen by using chloroform and determine the mass of extracted kerogen.

Step 106: determine a difference between the mass of the oven-dried kerogen and the mass of the extracted kerogen as the mass of oil in an organic matter, and record the mass of the oil in the organic matter as $m_{ai}$ (unit, g).

Step 107: multiply a ratio of the mass $m_{ai}$ of the oil in the organic matter to the mass $m_2$ of the second shale sample by 100 to obtain the mass of the oil in the organic matter of the shale sample, which is referred to as "A" (unit, %).

Step 108: subtract the mass of the oil in the organic matter of the shale sample from the total content of the shale oil in the shale to obtain the mass of the oil in the inorganic mineral of the shale, which is referred to as "A" (unit, %).

The treatment results of the 15 samples are shown in Table 2. In Table 2, the type represents the type of the kerogen, $R_o$ represents the VR, and TOC represents the TOC of the sample.

TABLE 2

Geochemical data and calculated hydrocarbon content in the inorganic part of 15 samples

| Well No. | Depth (m) | Type | $R_o$ (%) | TOC (%) | Porosity (%) | Total "A" (%) | Organic "A" (%) | Inorganic "A" (%) | Organic "A"/ Inorganic "A" |
|---|---|---|---|---|---|---|---|---|---|
| Gu 204 | 2376 | II1 | 1.49 | 1.47 | 6.42 | 0.58 | 0.31 | 0.27 | 0.85 |
| Gu 844 | 2579 | II2 | 1.79 | 1.6 | 5.46 | 0.23 | 0.04 | 0.19 | 5.43 |
| Ying 391 | 2166 | II2 | 1.22 | 0.45 | 7.59 | 0.13 | 0.02 | 0.1 | 4.9 |
| Ying 52 | 2187.3 | II1 | 1.25 | 1.56 | 7.47 | 0.78 | 0.18 | 0.6 | 3.39 |
| Ying 52 | 2189 | II1 | 1.25 | 3.76 | 7.46 | 0.92 | 0.75 | 0.17 | 0.22 |
| Ying 52 | 2190.35 | II1 | 1.25 | 2.67 | 7.45 | 0.77 | 0.21 | 0.56 | 2.72 |
| Ying 52 | 2190.6 | II1 | 1.25 | 1.46 | 7.45 | 0.37 | 0.13 | 0.24 | 1.85 |
| Tai 602 | 1821 | I | 0.89 | 2.41 | 10.01 | 0.72 | 0.22 | 0.5 | 2.21 |
| Tai 602 | 1825.5 | I | 0.89 | 4.52 | 9.97 | 0.83 | 0.31 | 0.52 | 1.68 |
| Tai 602 | 1827 | I | 0.89 | 3.77 | 9.96 | 1.18 | 0.4 | 0.78 | 1.95 |
| Xu 11 | 1948 | I | 0.99 | 2.64 | 9.04 | 0.89 | 0.53 | 0.36 | 0.68 |
| Xu 11 | 1965.47 | I | 1.01 | 1.79 | 8.92 | 0.33 | 0.26 | 0.07 | 0.26 |
| Xu 11 | 1966.27 | I | 1.01 | 3.32 | 8.91 | 0.73 | 0.36 | 0.37 | 1 |
| Xu 11 | 1972 | I | 1.02 | 3.31 | 8.87 | 0.62 | 0.42 | 0.19 | 0.46 |
| Xu 11 | 1996.17 | I | 1.04 | 5.27 | 8.70 | 1.23 | 1.03 | 0.2 | 0.19 |

Step 109: fit the ratio of the mass of the oil in the inorganic mineral of the shale to the mass of the oil in the organic matter of the shale sample and the parameter of the shale sample to establish a model for predicting the ratio of the mass of the oil in the inorganic mineral of the shale to the mass of the oil in the organic matter.

The ratio of the inorganic "A" to the organic "A" ($W_{inorganic/organic}$), the quartz ratio, the clay mineral ratio, other mineral ratios (including a carbonate mineral ratio and a heavy mineral ratio), the TOC, the VR $R_o$ and the porosity $\Phi$ were fit by using matrix laboratory (MATLAB) to establish a $W_{inorganic/organic}$ prediction model. Undetermined parameters such as $M_{TOC}$, $M_q$, $M_c$, $M_o$, a, b, $d_1$ and $d_2$ in the prediction model were optimized, as shown in Table 3.

The prediction model was calculated by:

$$W_{inorganic/organic} = \frac{1}{\sqrt{2\pi} \cdot (d_1 + d_2)} (M_{TOC} \cdot TOC + M_q \cdot Quanrtz + M_c \cdot Clay + M_0 \cdot Other) \cdot$$

$$EXP\left[-\left(\frac{\ln R_0 - a}{d_1}\right)^2 - \left(\frac{\ln \Phi - b}{d_2}\right)^2\right]$$

where, $W_{inorganic/organic}$ indicates a ratio of the mass of the oil in the inorganic mineral of the shale to the mass of the oil in the organic matter of the shale sample; TOC indicates a total organic carbon content; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient; Other indicates other ratios, such as a carbonate mineral ratio; $R_o$ indicates a VR; a indicates a first VR coefficient; $d_1$ indicates a second VR coefficient; $\Phi$ indicates a porosity; b indicates a first porosity coefficient; $d_2$ indicates a second porosity coefficient.

TABLE 3

Optimization results of parameters in the model

| Type | $M_{TOC}$ | $M_q$ | $M_c$ | $M_o$ | a | b | $d_1$ | $d_2$ |
|---|---|---|---|---|---|---|---|---|
| I | 3.93 | 1.67 | −2.86 | −0.75 | −0.27 | 2.41 | −9.20 | −0.18 |
| II | −0.60 | 0.76 | −0.72 | 0.00 | −0.75 | 2.89 | −1.12 | −1.12 |

Step 110: obtain the mass of oil in an organic matter of shale to be detected.

Figure 2:
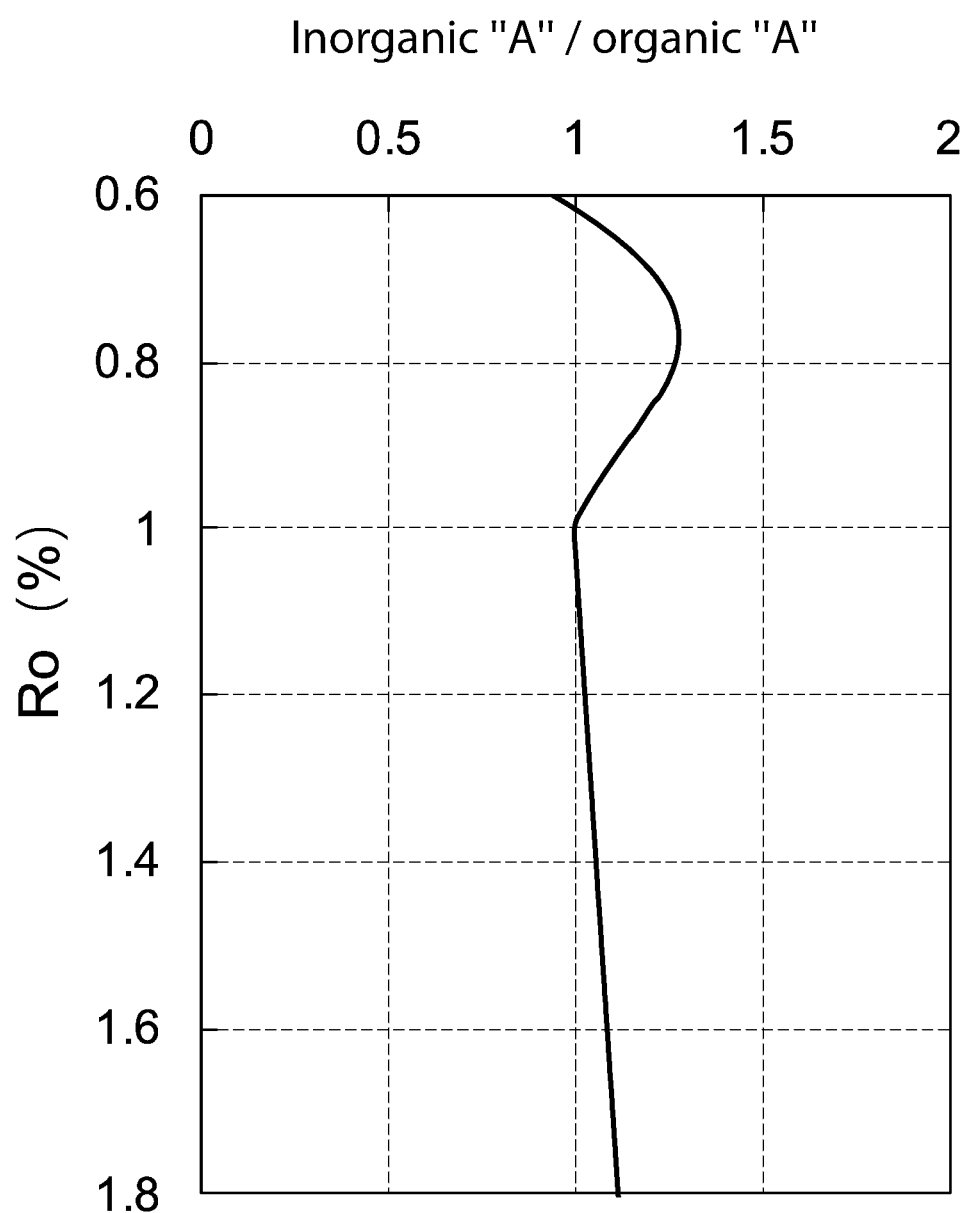
FIG. 2 is a graphical plot showing an evolution trend of an inorganic "A"/organic "A" ratio with $R_o$ according to another embodiment.

Taking the inorganic mineral composition of the shale of deep lake to semi-deep lake facies in the Qing-1 Member of the Songliao Basin as an example, the average quartz ratio was 32.6%, the average clay mineral ratio as 37.2%, and the other average mineral ratio was 29.5%. Together with TOC=5%, these data were substituted into the $W_{inorganic/organic}$ prediction model obtained in step 109 to calculate the inorganic "A"/organic "A" ratio of the deep lake to semi-deep lake facies, as shown in FIG. 2, which shows an evolution trend of the inorganic "A"/organic "A"

ratio with $R_o$. As can be seen from FIG. 2 that the inorganic "A"/organic "A" ratio tends to increase first and then decrease and then increase with the increase of $R_o$, and the maximum value, i.e. 1.281, is at a low maturity stage.

Step 111: use the prediction model to determine the mass of the oil in an inorganic mineral of the shale to be detected according to the mass of the oil in the organic matter of the shale to be detected.

Step 111 specifically includes: determine the mass of the oil in the inorganic mineral of the shale to be detected according to the following formula:

$$Q_{inorganic} = Q_{organic} \times W_{inorganic/organic}$$

where, $Q_{inorganic}$ indicates the mass of the oil in the inorganic mineral of the shale to be detected, mg/g TOC, and $Q_{organic}$ indicates the mass of the oil in the organic matter of the shale to be detected.

Figure 3:
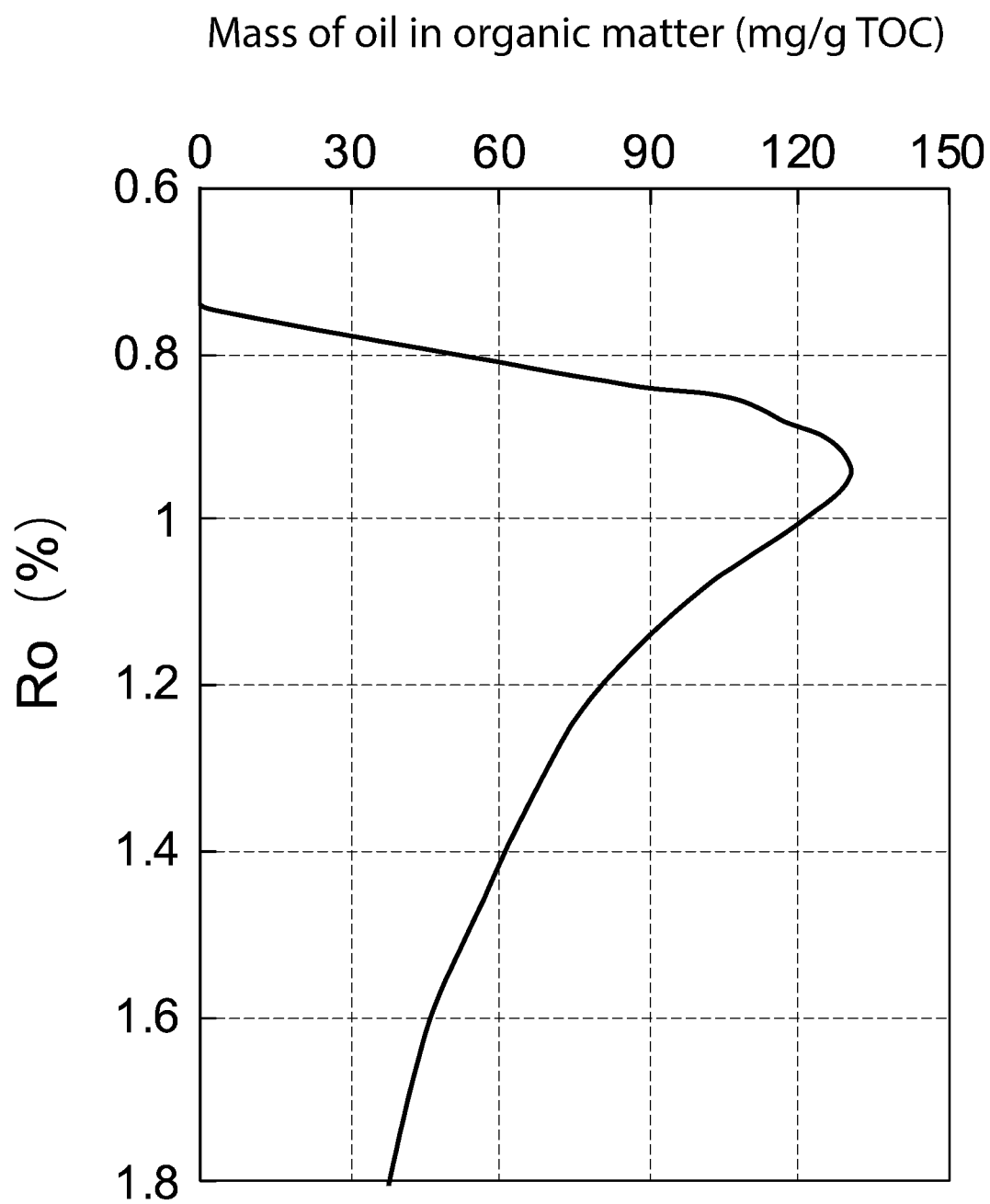
FIG. 3 is a graphical plot showing an evolution trend of the mass of oil in an organic matter of shale with Ro according to a further embodiment.
Figure 4:
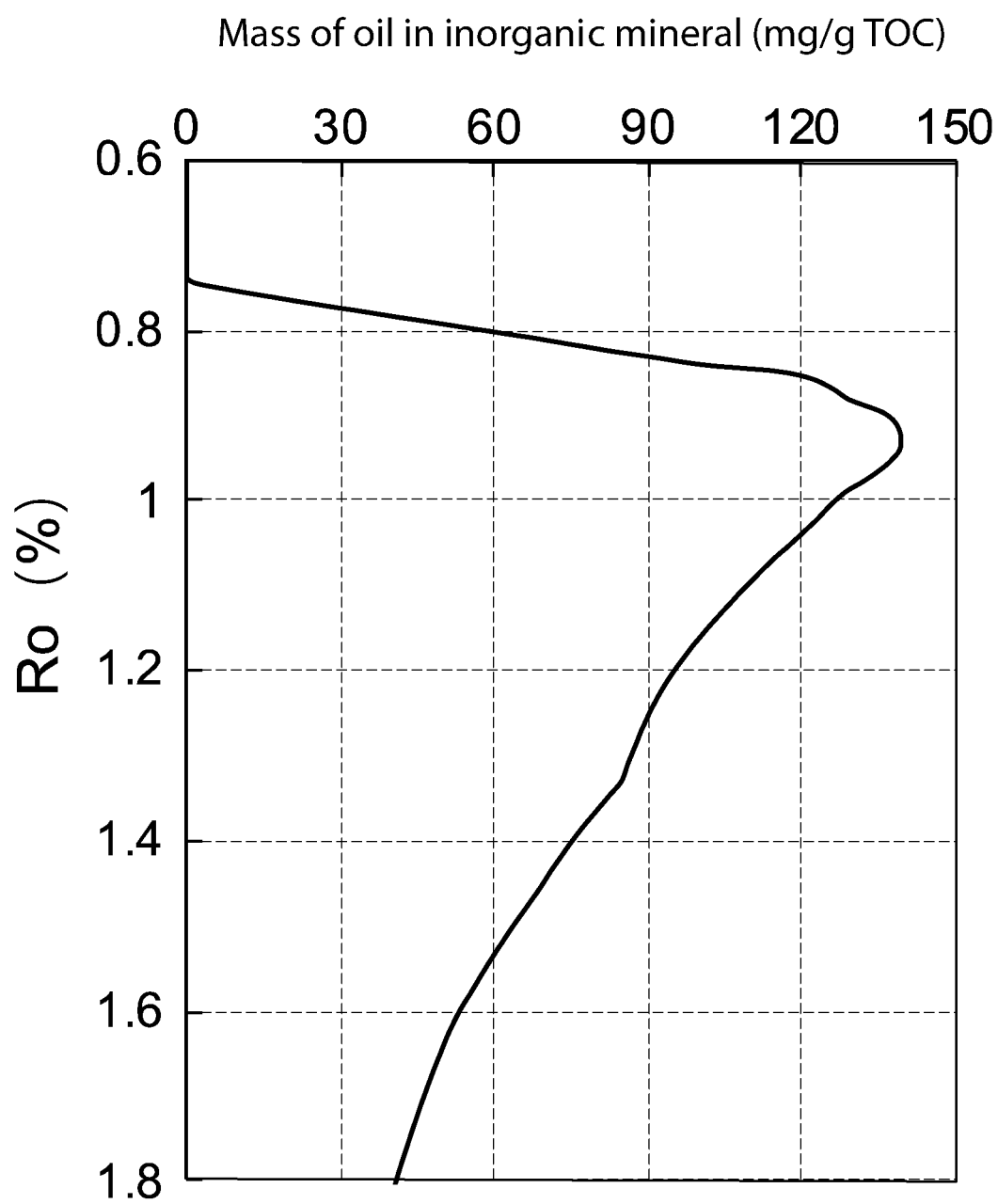
FIG. 4 is a graphical plot showing an evolution trend of the mass of oil in an inorganic mineral of shale with Ro according to another embodiment.

FIG. 3 shows an evolution trend of the mass of the oil in the organic matter of the shale with $R_o$. FIG. 4 shows an evolution trend of the mass of the oil in the inorganic mineral of the shale with $R_o$. As can be seen from FIG. 4 that the mass of the shale oil in the inorganic part increases first and then decreases with $R_o$, and the maximum value is 139.187 mg/g TOC.

Figure 5:
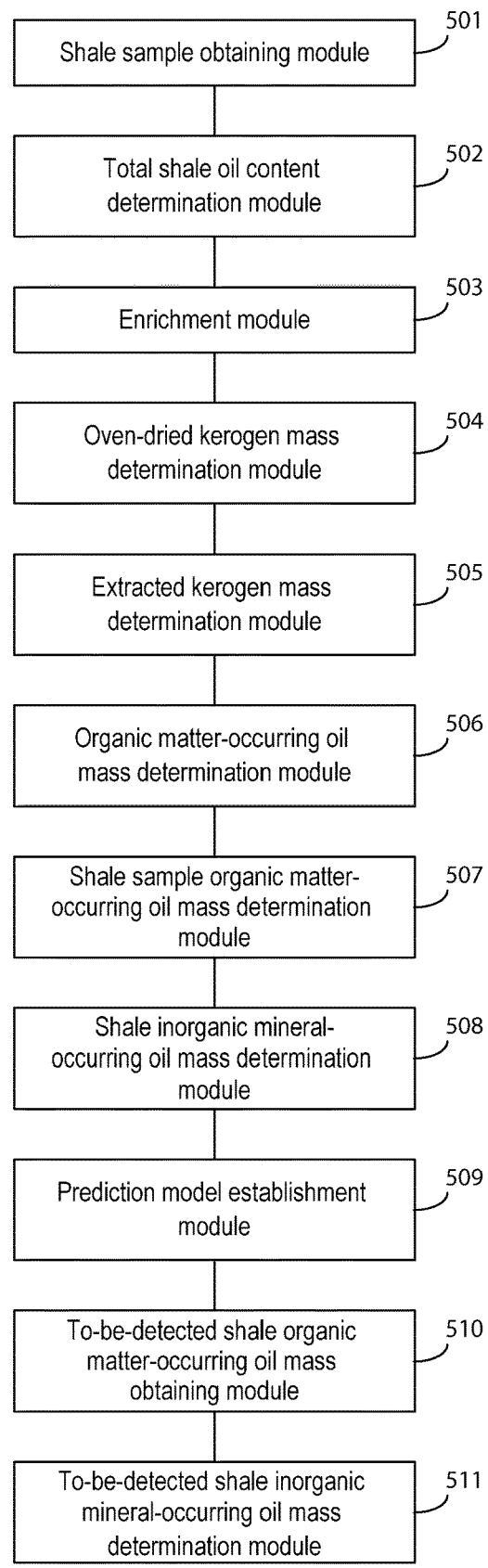
FIG. 5 is a schematic structural diagram of a system for detecting the mass of oil in an inorganic mineral of shale according to embodiments of the present invention.

FIG. 5 is a structural diagram of a system for detecting the mass of oil in an inorganic mineral of shale according to an example of the present invention. As shown in FIG. 5, a system for detecting the mass of oil in an inorganic mineral of shale includes a shale sample obtaining module, a total shale oil content determination module, an enrichment module, an oven-dried kerogen mass determination module, an extracted kerogen mass determination module, an organic matter-occurring oil mass determination module, a shale sample organic matter-occurring oil mass determination module, a shale inorganic mineral-occurring oil mass determination module, a prediction model establishment module, a to-be-detected shale organic matter-occurring oil mass obtaining module and a to-be-detected shale inorganic mineral-occurring oil mass determination module.

The shale sample obtaining module 501 is configured to obtain a shale sample and determine a parameter of the shale sample. The parameter includes a mineral composition ratio, a TOC content, a VR and a porosity; the mineral composition ratio includes a quartz ratio, a clay mineral ratio and a carbonate mineral ratio.

The total shale oil content determination module 502 is configured to divide the shale sample into a first shale sample and a second shale sample, and perform an extraction test on the first shale sample by using chloroform to obtain a total content of shale oil in the shale.

The enrichment module 503 is configured to enrich kerogen from the second shale sample to obtain dry kerogen.

The oven-dried kerogen mass determination module 504 is configured to oven-dry the dry kerogen to obtain oven-dried kerogen and determine the mass of the oven-dried kerogen.

The extracted kerogen mass determination module 505 is configured to perform an extraction test on the oven-dried kerogen by using chloroform and determine the mass of extracted kerogen.

The organic matter-occurring oil mass determination module 506 is configured to determine a difference between the mass of the oven-dried kerogen and the mass of the extracted kerogen as the mass of oil in an organic matter.

The shale sample organic matter-occurring oil mass determination module 507 is configured to multiply a ratio of the mass of the oil in the organic matter to the mass of the second shale sample by 100 to obtain the mass of the oil in the organic matter of the shale sample.

The shale inorganic mineral-occurring oil mass determination module 508 is configured to subtract the mass of the oil in the organic matter of the shale sample from the total content of the shale oil in the shale to obtain the mass of the oil in the inorganic mineral of the shale.

The prediction model establishment module 509 is configured to fit the ratio of the mass of the oil in the inorganic mineral of the shale to the mass of the oil in the organic matter of the shale sample and the parameter of the shale sample to establish a model for predicting the ratio of the mass of the oil in the inorganic mineral of the shale to the mass of the oil in the organic matter.

The prediction model is calculated by:

$$W_{inorganic/organic} = \frac{1}{\sqrt{2\pi} \cdot (d_1 + d_2)} (M_{TOC} \cdot TOC + M_q \cdot Quanrtz + M_c \cdot Clay + M_0 \cdot Other) \cdot EXP\left[-\left(\frac{\ln R_0 - a}{d_1}\right)^2 - \left(\frac{\ln \Phi - b}{d_2}\right)^2\right]$$

where, $w_{inorganic/organic}$ indicates a ratio of the mass of the oil in the inorganic mineral of the shale to the mass of the oil in the organic matter of the shale sample; TOC indicates a total organic carbon content; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient; Other indicates other ratios, such as a carbonate mineral ratio; $R_o$ indicates a VR; a indicates a first VR coefficient; $d_1$ indicates a second VR coefficient; $\Phi$ indicates a porosity; b indicates a first porosity coefficient; $d_2$ indicates a second porosity coefficient.

The to-be-detected shale organic matter-occurring oil mass obtaining module 510 is configured to use the prediction model to determine the mass of oil in an organic matter of shale to be detected.

The to-be-detected shale inorganic mineral-occurring oil mass determination module 511 is configured to use the prediction model to determine the mass of the oil in an inorganic mineral of the shale to be detected according to the mass of the oil in the organic matter of the shale to be detected.

The to-be-detected shale inorganic mineral-occurring oil mass determination module 511 specifically includes: a to-be-detected shale inorganic mineral-occurring oil mass determination unit, configured to determine the mass of the oil in the inorganic mineral of the shale to be detected according to the following formula:

$$Q_{inorganic} = Q_{organic} \times W_{inorganic/organic}$$

where, $Q_{inorganic}$ indicates the mass of the oil in the inorganic mineral of the shale to be detected, and $Q_{organic}$ indicates the mass of the oil in the organic matter of the shale to be detected.

For a system disclosed in the examples, since it corresponds to the method disclosed in the examples, the description is relatively simple, and reference can be made to the method description.

In this paper, several examples are used for illustration of the principles and implementations of the present invention. The description of the foregoing examples is used to help illustrate the method of the present invention and the core principles thereof. In addition, those of ordinary skill in the art can make various modifications in terms of specific implementations and scope of application in accordance with the teachings of the present invention. In conclusion, the content of this specification shall not be construed as a limitation to the present invention.

The embodiments described above are only descriptions of preferred embodiments of the present invention, and are not intended to limit the scope of the present invention. Various variations and modifications can be made to the technical solution of the present invention by those of ordinary skill in the art, without departing from the design and spirit of the present invention. The variations and modifications should all fall within the claimed scope defined by the claims of the present invention.

What is claimed is:

1. A method for detecting a mass of oil in an inorganic mineral of shale, comprising:
   obtaining a shale sample and determining a parameter of the shale sample;
      wherein the parameter comprises a mineral composition ratio, a total organic carbon (TOC) content, a vitrinite reflectance (VR) and a porosity;
      the mineral composition ratio is derived by performing whole-rock X-ray diffraction (XRD) on the shale sample; and
      the mineral composition ratio comprises a quartz ratio, a clay mineral ratio and a carbonate mineral ratio;
   dividing the shale sample into a first shale sample and a second shale sample, and performing an extraction test on the first shale sample by using chloroform to obtain a total content of shale oil in the shale;
   enriching kerogen from the second shale sample to obtain dry kerogen, specifically comprising: enriching the kerogen in the second shale sample by using a sedimentary rock kerogen separation method;
   oven-drying the dry kerogen to obtain oven-dried kerogen and determining the mass of the oven-dried kerogen, specifically comprising: drying the dry kerogen by using an oven at 110° C. for 6 h;
   performing an extraction test on the oven-dried kerogen by using chloroform and determining a mass of extracted kerogen;
   determining a difference between the mass of the oven-dried kerogen and the mass of the extracted kerogen as the mass of oil in an organic matter;
   multiplying a ratio of the mass of the oil in the organic matter to the mass of the second shale sample by 100 to obtain the mass of the oil in the organic matter of the shale sample;
   subtracting the mass of the oil in the organic matter of the shale sample from the total content of the shale oil in the shale to obtain the mass of the oil in the inorganic mineral of the shale;
   fitting the ratio of the mass of the oil in the inorganic mineral of the shale to the mass of the oil in the organic matter of the shale sample and the parameter of the shale sample to establish a model for predicting the ratio of the mass of the oil in the inorganic mineral of the shale to the mass of the oil in the organic matter;
   obtaining the mass of oil in an organic matter of shale to be detected; and
   using the prediction model to determine the mass of the oil in an inorganic mineral of the shale to be detected according to the mass of the oil in the organic matter of the shale to be detected.

2. The method of claim 1, wherein the prediction model is calculated by:

$$W_{inorganic/organic} = \frac{1}{\sqrt{2\pi} \cdot (d_1 + d_2)} (M_{TOC} \cdot TOC + M_q \cdot \text{Quanrtz} + M_c \cdot \text{Clay} + M_0 \cdot \text{Other}) \cdot \text{EXP}\left[-\left(\frac{\ln R_0 - a}{d_1}\right)^2 - \left(\frac{\ln \Phi - b}{d_2}\right)^2\right]$$

wherein, $W_{inorganic/organic}$ indicates a ratio of the mass of the oil in the inorganic mineral of the shale to the mass of the oil in the organic matter of the shale sample; TOC indicates a total organic carbon content; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient; Other indicates other ratios, such as a carbonate mineral ratio; $R_o$ indicates a VR; a indicates a first VR coefficient; $d_1$ indicates a second VR coefficient; $\Phi$ indicates a porosity; b indicates a first porosity coefficient; $d_2$ indicates a second porosity coefficient.

3. The method of claim 2, wherein the step of using the prediction model to determine the mass of the oil in an inorganic mineral of the shale comprises:
   determining the mass of the oil in the inorganic mineral of the shale to be detected according to the following formula:

$$Q_{inorganic} = Q_{organic} \times W_{inorganic/organic}$$

wherein, $Q_{inorganic}$ indicates the mass of the oil in the inorganic mineral of the shale to be detected, and $Q_{organic}$ indicates the mass of the oil in the organic matter of the shale to be detected.

4. A system for detecting a mass of oil in an inorganic mineral of shale, comprising:
   a shale sample obtaining module, configured to obtain a shale sample and determine a parameter of the shale sample;
      wherein the parameter comprises a mineral composition ratio, a total organic carbon (TOC) content, a vitrinite reflectance (VR) and a porosity;
      the mineral composition ratio is derived by performing whole-rock X-ray diffraction (XRD) on the shale sample; and
      the mineral composition ratio comprises a quartz ratio, a clay mineral ratio and a carbonate mineral ratio;
   a total shale oil content determination module, configured to divide the shale sample into a first shale sample and a second shale sample and perform an extraction test on the first shale sample by using chloroform to obtain a total content of shale oil in the shale;
   an enrichment module, configured to enrich kerogen from the second shale sample by using a sedimentary rock kerogen separation method to obtain dry kerogen;
   an oven-dried kerogen mass determination module, configured to oven-dry the dry kerogen by using an oven at 110° C. for 6 h to obtain oven-dried kerogen and determine a mass of the oven-dried kerogen;
   an extracted kerogen mass determination module, configured to perform an extraction test on the oven; dried kerogen by using chloroform and determine the mass of extracted kerogen;

an organic matter-occurring oil mass determination module, configured to determine a difference between the mass of the oven-dried kerogen and the mass of the extracted kerogen as the mass of oil in an organic matter;

a shale sample organic matter-occurring oil mass determination module, configured to multiply a ratio of the mass of the oil in the organic matter to the mass of the second shale sample by 100 to obtain the mass of the oil in the organic matter of the shale sample;

a shale inorganic mineral-occurring oil mass determination module, configured to subtract the mass of the oil in the organic matter of the shale sample from the total content of the shale oil in the shale to obtain the mass of the oil in the inorganic mineral of the shale;

a prediction model establishment module, configured to fit the ratio of the mass of the oil in the inorganic mineral of the shale to the mass of the oil in the organic matter of the shale sample and the parameter of the shale sample to establish a model for predicting the ratio of the mass of the oil in the inorganic mineral of the shale to the mass of the oil in the organic matter;

a to-be-detected shale organic matter-occurring oil mass obtaining module, configured to use the prediction model to determine the mass of the oil in an organic matter of shale to be detected; and a to-be-detected shale inorganic mineral-occurring oil mass determination module, configured to use the prediction model to determine the mass of the oil in an inorganic mineral of the shale to be detected according to the mass of the oil in the organic matter of the shale to be detected.

5. The system of claim 4, wherein the prediction model is calculated by:

$$W_{inorganic/organic} = \frac{1}{\sqrt{2\pi} \cdot (d_1 + d_2)} (M_{TOC} \cdot TOC + M_q \cdot \text{Quanrtz} + M_c \cdot \text{Clay} + M_0 \cdot \text{Other}) \cdot \text{EXP}\left[-\left(\frac{\ln R_0 - a}{d_1}\right)^2 - \left(\frac{\ln \Phi - b}{d_2}\right)^2\right]$$

wherein, $W_{inorganic/organic}$ indicates a ratio of the mass of the oil in the inorganic mineral of the shale to the mass of the oil in the organic matter of the shale sample; TOC indicates a total organic carbon content; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient; Other indicates other ratios, such as a carbonate mineral ratio; $R_o$ indicates a VR; a indicates a first VR coefficient; $d_1$ indicates a second VR coefficient; $\Phi$ indicates a porosity; b indicates a first porosity coefficient; $d_2$ indicates a second porosity coefficient.

6. The system of claim 5, wherein the to-be-detected shale inorganic mineral-occurring oil mass determination module comprises:

a to-be-detected shale inorganic mineral-occurring oil mass determination unit, configured to determine the mass of the oil in the inorganic mineral of the shale to be detected according to the following formula:

$$Q_{inorganic} = Q_{organic} \times W_{inorganic/organic}$$

wherein, $Q_{inorganic}$ indicates the mass of the oil in the inorganic mineral of the shale to be detected, and $Q_{organic}$ indicates the mass of the oil in the organic matter of the shale to be detected.

* * * * *